United States Patent
Segura et al.

(10) Patent No.: US 7,240,553 B2
(45) Date of Patent: Jul. 10, 2007

(54) NON-INVASIVE DETECTION AND ANALYSIS OF MICROORGANISMS IN DIARY PRODUCTS PACKAGED IN PAPER OR PAPERBOARD BASED LAMINATED RECIPIENTS USING DRY COUPLING ELASTIC WAVES

(75) Inventors: Luis Elvira Segura, Madrid (ES); Francisco Montero de Espinosa Freijo, Madrid (ES); Pablo Resa López, Madrid (ES); Yago Gomez-Ullate Ricon, Madrid (ES)

(73) Assignees: Consejo Superior De Investigaciones Cientificas (CSIC), Serrano, Madrid (ES); Corporacion Alimentaria Penasanta, S. A. (ES)

( * ) Notice: Subject to any disclaimer, the term of this patent is extended or adjusted under 35 U.S.C. 154(b) by 162 days.

(21) Appl. No.: 11/010,662

(22) Filed: Dec. 13, 2004

(65) Prior Publication Data

US 2005/0115323 A1 Jun. 2, 2005

(30) Foreign Application Priority Data

| Jun. 14, 2002 | (ES) | 200201378 |
| May 5, 2003 | (ES) | 200301010 |
| Jun. 3, 2003 | (ES) | ES03/00287 |

(51) Int. Cl.
  *G01N 29/14* (2006.01)
(52) U.S. Cl. ............... 73/597; 73/52; 73/64.53
(58) Field of Classification Search ........... 73/596, 73/290 V, 61.75, 599, 602, 61.79, 64.53, 73/598, 600, 597, 52
  See application file for complete search history.

(56) References Cited

U.S. PATENT DOCUMENTS

| 4,384,476 | A | * | 5/1983 | Black et al. ............ 73/61.79 |
| 5,861,548 | A | * | 1/1999 | Melvin et al. ............ 73/52 |
| 5,929,337 | A | * | 7/1999 | Collins et al. ............ 73/597 |
| 6,295,873 | B1 |   | 10/2001 | Condreva |
| 6,324,901 | B1 |   | 12/2001 | Fluh et al. |
| 6,338,272 | B1 | * | 1/2002 | Heuft et al. ............ 73/290 V |
| 6,513,385 | B1 | * | 2/2003 | Han et al. ............ 73/629 |
| 6,591,680 | B2 | * | 7/2003 | Batzinger et al. ............ 73/598 |
| 6,595,061 | B2 | * | 7/2003 | Gorman et al. ............ 73/597 |
| 6,631,639 | B1 | * | 10/2003 | Dam et al. ............ 73/290 V |
| 6,782,752 | B2 | * | 8/2004 | Basir et al. ............ 73/625 |
| 6,938,488 | B2 | * | 9/2005 | Diaz et al. ............ 73/597 |

FOREIGN PATENT DOCUMENTS

| ES | 0269815 | 6/1988 |
| ES | 2147149 | 8/2000 |
| JP | 1214758 | 8/1989 |
| RO | 117213 | 11/2001 |

* cited by examiner

*Primary Examiner*—Hezron Williams
*Assistant Examiner*—Jacques M. Saint-Surin
(74) *Attorney, Agent, or Firm*—John C. McMahon (57) ABSTRACT

The invention relates to a method and a device for the early detection of the presence of micro-organisms in food, particularly in milk and derivatives thereof. One of the main advantages of the invention lies in the fact that the aforementioned detection method can be performed inside the commercial packaging thereof without the need for said packaging to be opened. The presence of micro-organism is detected, before they can produce drastic changes in the physical properties of the product, according to changes in the propagation of elastic waves (velocity, attenuation and harmonic distortion) through the product and, moreover, different types of micro-organisms can be distinguished. The inventive detection method is performed under dry conditions and requires an environment with controlled humidity and temperature.

13 Claims, 6 Drawing Sheets

NON-INVASIVE DETECTION AND ANALYSIS OF MICROORGANISMS IN DIARY PRODUCTS PACKAGED IN PAPER OR PAPERBOARD BASED LAMINATED RECIPIENTS USING DRY COUPLING ELASTIC WAVES

FIELD OF THE ART

The problem of food safety and quality control of foods is a topic of growing interest in our society, due to the direct effect it has on the health of the consumers. In particular, milk and its derivatives constitute an essential part of the human diet from the earliest age. As a result, to provide fast and reliable quality control systems for these products is of great importance for the dairy industry.

Milk is an ideal substrate for bacterial growth due to the large amount of nutrients it has. Furthermore, since it is an animal product subjected to a great diversity of production methods, it can be contaminated with a broad spectrum of microorganisms. In fact, the occurrence of bacterial infections in the production process of dairy products, which invalidate them for human consumption, is usual. For this reason, within the quality control of dairy product production, microbiological detection plays the most important role. Furthermore, an early and efficient detection of the presence of microorganisms in these products gives important economic benefits resulting from an early stopping of a contaminated production to prevent producing foods which might be discarded once the presence of these microorganisms were detected. Furthermore, circulating capital costs are reduced by reducing the prepared product storage time kept for foreseeing any incident.

STATE OF THE ART

There is a wide variety of systems for microbial detection in dairy products (R. K. Robinson. Microbiologia Lactológica (*Dairy Microbiology*), Vol (I and II). Ed. Acribia S. A., Zaragoza, Spain (1987)). The bacterial load is a function of the number and the bacteria species present. A suitable bacterial control program must include direct measurements, which involve microbial count. However, this type of processes entails an important waste of time and money. As a result, the dairy industry usually selects indirect quality tests based on the metabolic activity of the different microorganisms present. Some of the most commonly used tests are described below.

Among the direct methods there are:

Total microflora by culture: The samples of milk are diluted and inoculated in plates containing a culture medium, such as agar or triptone, then they are incubated and, finally, the colonies are counted.

Direct microscopy count (breed method): 0.01 to 0.05 ml of milk are spread on a slide in a 1 to 4 $cm^2$ area; it is dried, degreased with xylol, fixed with alcohol and dyed with 0.3% methylene blue.

Investigation for determining microbial groups, specific tests are carried out according to the microbial group to be detected (Coliform bacteria, heat-resistant microorganisms, sporulated anaerobic bacteria, gas producers, . . . ).

Among the indirect methods there are:

Pressure: detection of the increase of pressure in containers due to the gaseous production resulting from the metabolism of certain microorganisms.

Acidity and pH: direct measurement of these parameters, modified during the metabolism of microorganisms.

Coagulation: the presence of coagulation is detected in milk when it is mixed with alcohol, boiled or incubated at a temperature between 30–37° C. for 12–24 hours.

Electrical impedance measurement: measurement of the variations in the real and imaginary part of the conductivity of a liquid substrate inoculated with milk. These variations clearly show the changes of the electric parameters of the substrate introduced by the growth of microorganisms.

Therefore, there is a wide variety of techniques for microbiological quality control, their suitability for being applied to the production process being assessed according to their rapidness, reliability and cost. However, they all have the common feature of being destructive processes: it is necessary to take a sample of the product at a given moment, opening the container. This implies the troublesome drawback of increasing the possibility of false positives due to subsequent contamination of the sample taken, as well as the necessity to wait for the sample incubation, which is sometimes an excessively long time, to ensure the sterility of the milk. Only a large increase of the pressure in flexible containers (which swell) or the occurrence of disintegration and coagulates in transparent containers (increasingly less used) give indications of the possible presence of microorganisms without opening the container. However, the main cases of deterioration of dairy products due to the presence of microorganisms, very important due to their frequency and consequences, fall outside these cases.

The measurement of the propagation parameters of elastic waves through a certain medium is being more and more widely used in quality control in the food industry (D. J. McClements. Ultrasonic characterization of foods and drinks: Principles, Methods and Applications. Critical reviews in Food Science and Nutrition 37 (1), 1–46, (1997)). The innocuous nature of this type of tests makes them suitable for the analysis of those substances whose preservation against any type of denaturation is highly important. Ultrasounds have been used in certain applications to determine the composition of foods exiting the production line by extracting a sample from the containers and introducing it in a measurement cell (J.W. Fitzgerald/Chesapeake Inst. Corp., U.S. Pat. No. 3,040,562, 1962).

There are works mentioning the use of ultrasounds for the detection of the degradation of packaged foods (Gestrelius, H., Mattila, T., Ahvenainen, R., Trends in Food Science and Technology 5 (12), 1991), using an acoustic streaming Doppler effect ultrasonic measuring technique. However, this technique has few possibilities of being able to be exploited industrially due to the difficulty of establishing a streaming in packaged foods in a controlled and repetitive manner. This is even more complicated in paper-based laminated containers which, due to their impedance decoupling with transduction systems, transmit only a small portion of the acoustic energy necessary both for measuring the Doppler effect and for establishing the streaming. Nor does it seem to be a very sensitive technique given that four days or more of incubation are needed so that the growth of microorganisms produces a detectable change in the sample. With a completely different concept, Ahvenainen et al. used echography for the detection of microorganisms (Ahvenainen, R, Mattila, T, Wirtanen, G; Lebensm.-Wiss. Technol. 22, 268–272 1989). This method has the drawback of not being suitable for the non-invasive detection in paperboard containers since, as they themselves state, it was necessary to change the product to another container to carry out the measurement. Furthermore, it is a method that is not readily applicable at an industrial level given the complexity and high price of echography systems. In a patent dated from the year 1987, M. Nagata et al. disclose an ultrasonic method for the detection of microorganisms in packaged products (Fujimori Kogyo Co. Ltd., EP 269,815). In the disclosed device, no thermostatting system is included, which introduces an important uncertainty in the system which the authors do not seem to warn about, since the ultrasonic propagation constants are highly sensitive with regard to the temperature. Likewise, the propagation measurement is carried out in a liquid bath, which is not suitable for containers with paper or paperboard components, which are degraded under these conditions.

DESCRIPTION OF THE INVENTION

The object of this patent is a new non-invasive method of broad spectrum microbiological detection and analysis based on the propagation of elastic waves through the milk or a dairy product derivative.

The market evolution demands the development of non-destructive methods capable of carrying out the microbiological evaluation of foods in any type of containers, including paper and paperboard laminated containers, which are increasingly more widespread. This entails the development of dry coupling detection systems, capable of detecting the slightest changes occurring in early phases of development of microorganisms in foods.

The changes detected in the propagation of the elastic wave can be due to several factors, which in turn will vary according to the microorganism or microorganisms present. This enables distinguishing between the different types of microorganisms which may contaminate dairy products. Among the most relevant causes for explaining the variations found in the wave propagation parameters are: the occurrence of gas in the medium, changes in the structure of the suspension due to modifications in the sizes of the fat globules or of the protein micelles, coagulation or gelation processes, precipitation of substances initially in suspension, or even the occurrence of a considerable number of microorganisms, which itself constitutes a change in the structure of the medium.

The process object of this patent shows the presence of microorganisms without extracting product samples from the interior of its commercial container. This feature prevents the product contamination during the microbiological quality control process. The invention enables the detection in any of the containers currently used in the dairy industry, including multilayer containers such as, for example, Combiblock and Tetrabrik-registered trademarks. Furthermore, by means of this method microbial growth can be monitored at the same time it is occurring, as the measurement is based on the continuous monitoring of the product. This feature enables the early detection of contaminations which can occur before the conventional incubation times pre-established for traditional microbiological control methods. With these, the product is checked after said incubation period, which could even exceed 48 hours.

The process (see FIGS. 1 and 2) consists of the automatic measurement of the parameters characterizing the propagation of a mechanical wave (amplitude, speed and harmonic distortion) through a dairy product-DP-contained in a recipient-RL. In turn, this process is based on a prior patent of a clinical process for the detection of microorganisms in biological fluids and clinical samples by means of the measurement of the propagation speed (Spanish patent ES 2 147 149). The measurement enclosure, ME, in which the product to be analyzed is located, must be suitably thermostatted (at the culture temperatures considered to be standard in the dairy industry), with an error of less than $0.1°$ C., for the purpose of preventing interferences between variations in the propagation of the mechanical wave due to a supposed microbial growth and those due to changes in the temperature of the medium.

Figure 1:
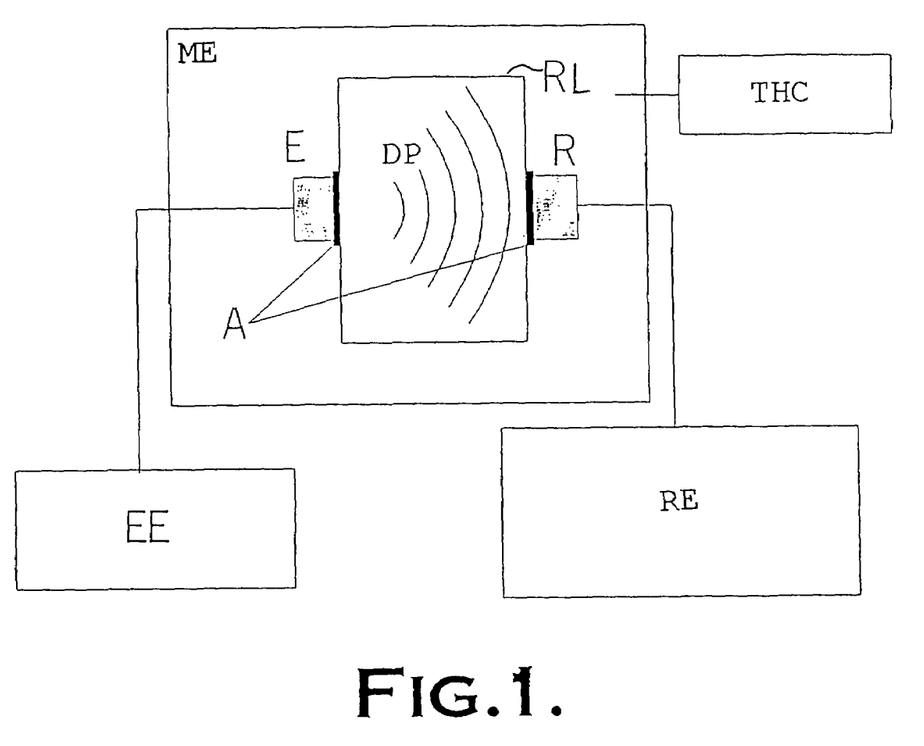
Figure 2:
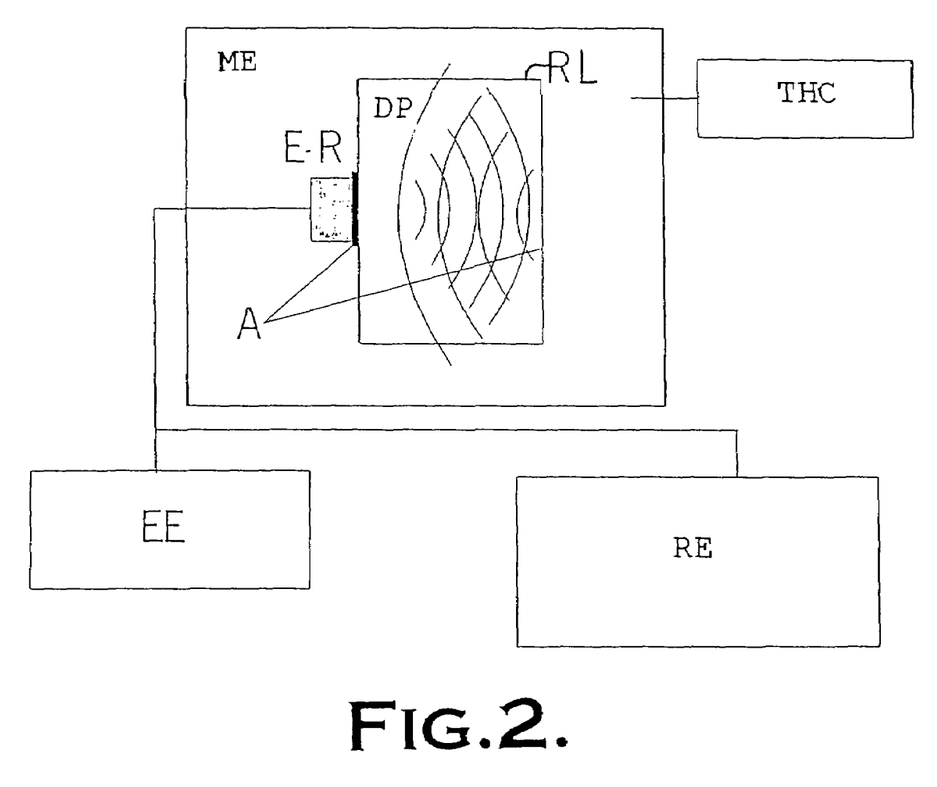

Unlike the reference (Spanish patent ES 2 147 149), the thermostatting must be carried out under dry conditions to prevent deterioration of the container. This detail is highly important since the features of the thermostatting system must be suitable for a gaseous medium; furthermore, humidity in this case constitutes another parameter that is capable of affecting the transmission of elastic waves through the recipient. The temperature and humidity control systems are shown in FIGS. 1 and 2 as THC. Unlike Spanish patent ES 2 147 149, the process includes the choice and generation of the working frequency—within the ultrasonic range—according to the type of container and product to be analyzed. The precision reached with this humidity and temperature control enables the detection of contaminations which do not drastically degrade the product, increasing the precision in the measurement of the propagation parameters compared to other ultrasonic methods, such as, for example, the mentioned patent (Fujimori Kogyo Co. Ltd. EP 269,815), in more than one order of magnitude.

Unlike ultrasonic systems of measurement in water, another key issue in this process is the incorporation of an element providing a suitable elastic coupling-C-between the elastic wave emission and reception systems and the recipient containing the dairy product. This coupling, whose geometry depends on the type of recipient, consists of a polymer with good elastic transmission properties (RTV silicon).

The measurement technique can use either the transmission-reception configuration with two facing transducers—E and R in FIG. 1—, or the pulse-echo configuration with a single transducer—E-R in FIG. 2—which emits the elastic wave and receives it after traversing the product and being reflected at the opposite side of the recipient. The emitter transducer—E in FIG. 1 and E–R in FIG. 2—is excited with an electronic system -EE- which generates an electrical signal, and the reception transducer—R in FIG. 1 and E-R in FIG. 2—will have an electronic stage for the processing of the received signal -ER-. In both cases, the elastic wave is processed after traversing the recipient and the product. To that end, the time difference between the triggering signal and the arrival of said pulse, the amplitude of the wave after traversing the medium and the change of the wave shape, are measured; unlike Spanish patent ES 2 147 149, in which only the change in the propagation speed is detected. The possible variation of one or several of these parameters provides information regarding the changes occurring in the dairy medium when it becomes colonized by microorganisms.

This measurement technique can be used for the microbiological quality control of another type of non-dairy liquid foods which may become a substrate for the growth of microorganisms similar to those occurring in dairy products, making the appropriate methodological modifications to adapt it to the problem in particular.

A commercial device carrying out this task will be constituted of a chamber provided with structural elements in which each of the containers, sensors and actuators for controlling the temperature and humidity and ultrasonic transducers for the emission and reception of elastic means will be independently housed. The detection device will also be provided with the electronic system necessary for the control of the temperature and humidity sensors and actuators, as well as for feeding the emission transducers and receiving the signal of the receiver transducers. Lastly, it is appropriate that the control of the electronic system be carried out through a computer system enabling the automation of said control, as well as the interpretation and storage of the data corresponding to the microbiological inspection tests. These systems will be described below.

a) Measurement Chamber

The main body of the measurement chamber will be constituted of a structure providing the suitable and stable thermal and hygroscopic conditions necessary for the measurement. The size will be designed according to the number of containers which will be housed in its interior for measurement. In addition to the function of isolation from the exterior, this chamber will house internal temperature and humidity control systems.

Independent housings for each container are arranged inside the main body of the chamber. These housings carry out the support function for the container, the thermal measurement and actuation systems and the ultrasonic transducers; enabling the independent microbiological inspection of each container.

b) Humidity and Temperature Control

The measurement chamber will have a humidity control system consisting of a humidity sensor and actuator. This system maintains the relative humidity in the chamber with variations of less than 1%.

Temperature control is preferably carried out by means of a double system. On one hand, the temperature of the general cavity is regulated through temperature sensors and thermal actuators. The temperature in the chamber is maintained slightly below the incubation temperature, a precision of ±0.1° C. being enough. On the other hand, an independent temperature control for each container is carried out at the incubation temperature with a precision of ±0.01° C., using sensors and actuators in contact with the container itself. These systems are installed in the individual container housing structures. The thermal control system is provided by electronic controllers placed out of the chamber, which enable programming a heating curve to minimize the time it takes the content of the container to go from room temperature to the incubation temperature without deteriorating the recipient or exceeding said incubation temperature.

c) Ultrasonic Transducers

Each housing is provided with a transducer (pulse-echo configuration) or a pair of piezoelectric transducers (emission-reception configuration) for the emission and reception of ultrasonic waves in a range between 100 kHz and 2 MHz. A multiple transducer system can also be used. The emitter or receiver surfaces of the transducers are provided with a layer made of an elastic polymer to obtain a good mechanical coupling to the container.

Each time a container is introduced in its housing and the microbiological inspection process beings, the ultrasonic transducers come into contact with the container, exerting a slight pressure on it through the elastic coupling layer. The transducers are positioned in parallel to one another, facing and fixed during the entire measurement process with allowances of less than 1 um.

d) Generation, Reception, Multiplexing and Thermal and Hygroscopic Control Electronics The control electronics can be included in the measurement chamber or be installed in modules separated therefrom.

The thermal and hygroscopic sensors are independently connected to their corresponding electronic controller circuits. In turn, these circuits are connected to the computer which controls the entire inspection process.

The signal generation system feeding the emitter ultrasonic transducers generate wave bursts whose central frequency corresponds to the central band of the transducers. The amplitude of said signal is adjusted according to the working frequency and the features of the container, contents and type of transducer used, in such a way that the wave picked up by the reception transducers has a signal/noise ratio high enough to be analyzed with the precision required for the measurement. Therefore it is appropriate to provide filtering and amplification stages for conditioning the reception signal which is generally a low amplitude and noisy signal. To carry out the analysis and interpretation of the signal, the latter is previously digitalized.

Each pair of emitter receiver transducers can be alternatively actuated through a multiplexer stage which is connected to the control computer. It is thus possible to relate a particular container with the information reaching the signal analysis and data interpretation system at all times.

Lastly and as repeatedly stated, a computer carries out the control of the entire inspection process; temperature, humidity, ultrasonic transducer multiplexing, emission and acquisition of the signals. The computer also carries out the processing, interpretation and storage, if necessary, of all the obtained data. All this is carried out through a specific software described in the following section.

e) Data Control and Interpretation

A software package manages the communication of the computer with the electronic equipment described, such that the inspection process is carried out independently for each container.

The software includes the mathematical processing of the signals picked up to obtain information regarding the condition of the contents of each container. For that, it incorporates an algorithm which enables interpreting the data received, giving rise to the occurrence of a warning when signs of deterioration are detected through the ultrasonic propagation measurement in a certain container.

The software enables storing the data and restarting each measurement channel when a new container is placed in a housing of the chamber.

EMBODIMENT EXAMPLE OF THE INVENTION

Example 1

Distinction Between Microorganisms

Figure 3:
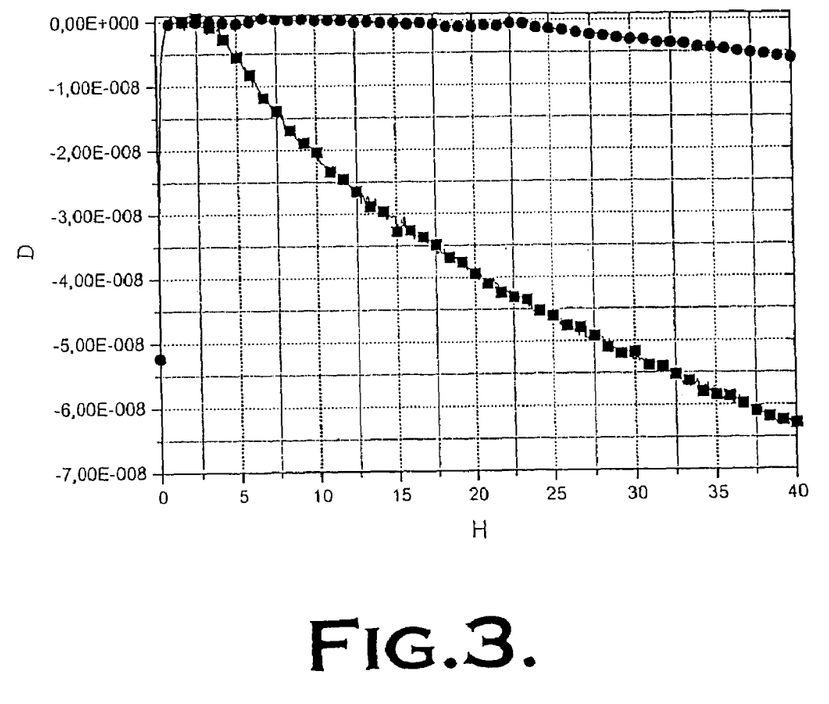

FIG. 3 shows the ultrasonic signal travel time delay after traversing milk inoculated with an initial concentration of about 100 cfu/ml of two different microorganisms, *Bacillus Cereus* (squares) and *Pseudomona Aeruginosa* (circles). In both cases, it can be seen how the delay decreases (which corresponds to an increase of the propagation speed). However, the presence of the microorganisms is detected at different times (after hour 3 in the case of *Bacillus Cereus* and after hour 23 in the case of *Pseudomona Aeruginosa*) and with an also different slope characterizing the nature of each of these contaminations.

Example 2

Figure 4:
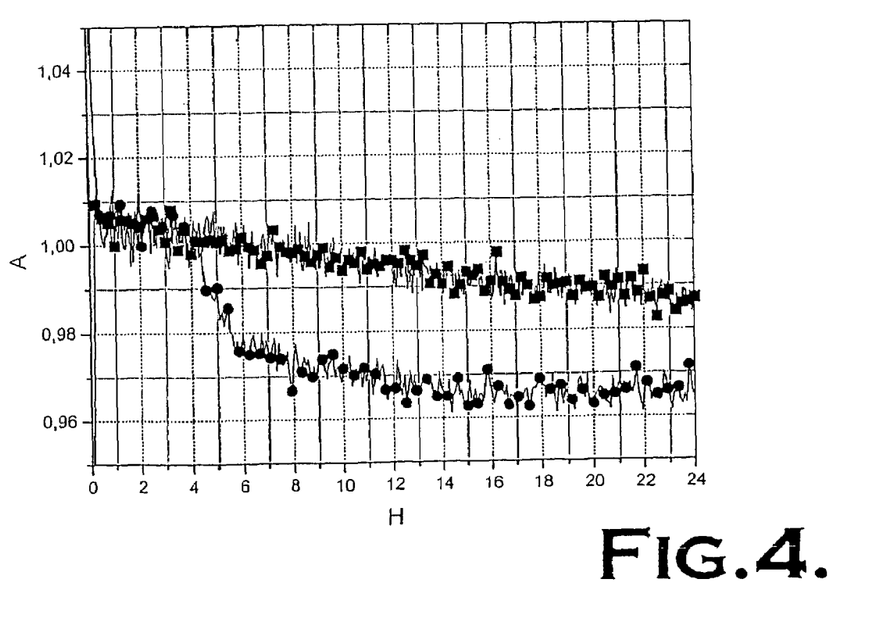

Application of the Measurement of the Amplitude of the Second Harmonic Distortion for Microbiological Detection The process object of this patent enables the detection of the microbiological presence not only through the measurement of travel times, but also with the measurement of amplitudes and harmonic distortion. Particularly in FIG. 4, the detection of the presence of *Bacillus Cereus* with the measurement of the second harmonic distortion is shown. Changes in said amplitude can be observed after hour 4, corresponding to the presence (circles) or not (squares) of *Bacillus Cereus* in milk. The level of second harmonic distortion reveals the deformation the wave is undergoing as it propagates through the medium.

Example 3

Microbiological Detection in Other Foods (Orange Juice)

FIG. 5 shows the application of the process to another liquid food, orange juice. The rapid deterioration occurring in the natural frozen orange juice after its thawing (circles) can be observed. This deterioration begins after the third hour, in contrast with the stability of the sterile UHT concentrated juice (squares). This detection was carried out through the measurement of the signal travel time.

Example 4

8-Channel Ultrasonic Device for the Detection of Microorganisms in Milk Packaged in Combibloc This device, whose scheme is shown in FIG. 6, consists of the elements described in the previous section, which are detailed below.

Measurement Chamber

The main body of the measurement chamber consists of a rigid structure manufactured in stainless steel. Eight individual housings (see FIG. 7) made of aluminum, inside of which the containers to be measured are placed, are coupled to this structure.

Humidity and Temperature Control in the Measurement Chamber

The measurement chamber has a humidity control system with a precision of ±1% relative humidity. The measurement chamber has a double temperature control system. The temperature control system of the general cavity consists of a temperature sensor and a Peltier effect thermal actuator. The temperature is maintained slightly below35° C. with a precision of ±0.1° C. The temperature control of each housing has an independent regulation system to optimize the heating time of the containers. The precision of this regulation is ±0.01° C.

Ultrasonic Transducers

The piezoelectric reception and emission transducers work at a resonance frequency of 800 kHz. These transducers are provided with an outer layer manufactured in an elastic polymer to obtain a good mechanical adaptation to the container, as can be observed in FIG. 8. One of the transducers is located at the door of the housing and the other one at the opposite wall. It is thus possible to comfortably introduce the container, the transducers remaining fixed and parallel to one another once the door of the corresponding housing is closed.

Generation and Reception Electronics

Each housing has a measurement channel made up of an emission transducer, a reception transducer and the corresponding connections. To alternatively actuate said channels, an electronic multiplexing stage is used. The signal generation system generates sine wave bursts with a signal amplitude of 5 V and central frequency corresponding to the band of the transducers. An oscilloscope is used to digitalize the reception signal. Lastly, a computer is used to carry out the control of the multiplexing, the acquisition of the signals, its processing and the obtention and evaluation of data. The interconnection of these systems is shown in the general scheme of the device (FIG. 6).

Control and Data Interpretation Software

The software manages the communication of the computer with the thermal controllers and the humidity control through a serial port with RS-485 protocol, with the multiplexer through another serial port with RS-232 protocol, and with the oscilloscope through a GPIB card, controlling the measurement process independently for each housing. The software includes the mathematical processing of the signals picked up to obtain information about the condition of the milk in each container. It also includes a graphic window and an algorithm which enables interpreting the data, giving rise to the occurrence of a warning when a sample with signs of deterioration is detected.

DESCRIPTION OF THE FIGURES

FIG. 1 shows a scheme of the measurement process in emission-reception configuration. It consists of the emitter transducer—E—and the receiver transducer—R—facing both sides of the recipient—RL—containing the dairy product—DP—.

The coupling of the transducers to the recipient is carried out through the polymer—A—. The measurement is carried out in an enclosure—ME—provided with a temperature and humidity control—THC—system. The emission transducer receives the signal from the electronic generation system—EE—and the signal received by the reception transducer is stored and processed by the reception electronics RE.

FIG. 2 shows the scheme of the measurement process in the pulse-echo configuration. It consists of the emitter-receiver—E-R—coupled to the recipient—RL—containing the dairy product—DP—through the polymer—A—. The measurement is carried out in an enclosure—ME—provided with a temperature and humidity control—TCM—system. The transducer receives the signal from the electronic generation system—EE—as well as the ultrasonic signal which reaches it after reflecting at the opposite side of the recipient, which is stored and processed by the receptions electronics RE.

FIG. 3 shows the delay of the ultrasonic signal after traversing milk contaminated with *Bacillus Cereus* (squares) and *Pseudomonas Aeruginosa* (circles). The H axis corresponds to the measurement time in hours and the R axis to the delay in seconds of the signal time-of-flight related to the time-of-flight of the initial signal.

FIG. 4 shows the amplitude of the second harmonic distortion signal after traversing sterile milk (squares) and milk contaminated with *Bacillus Cereus* (circles). The H axis corresponds to the measurement time in hours and the A axis to the normalized amplitude of the second harmonic distortion of the signal.

Figure 5:
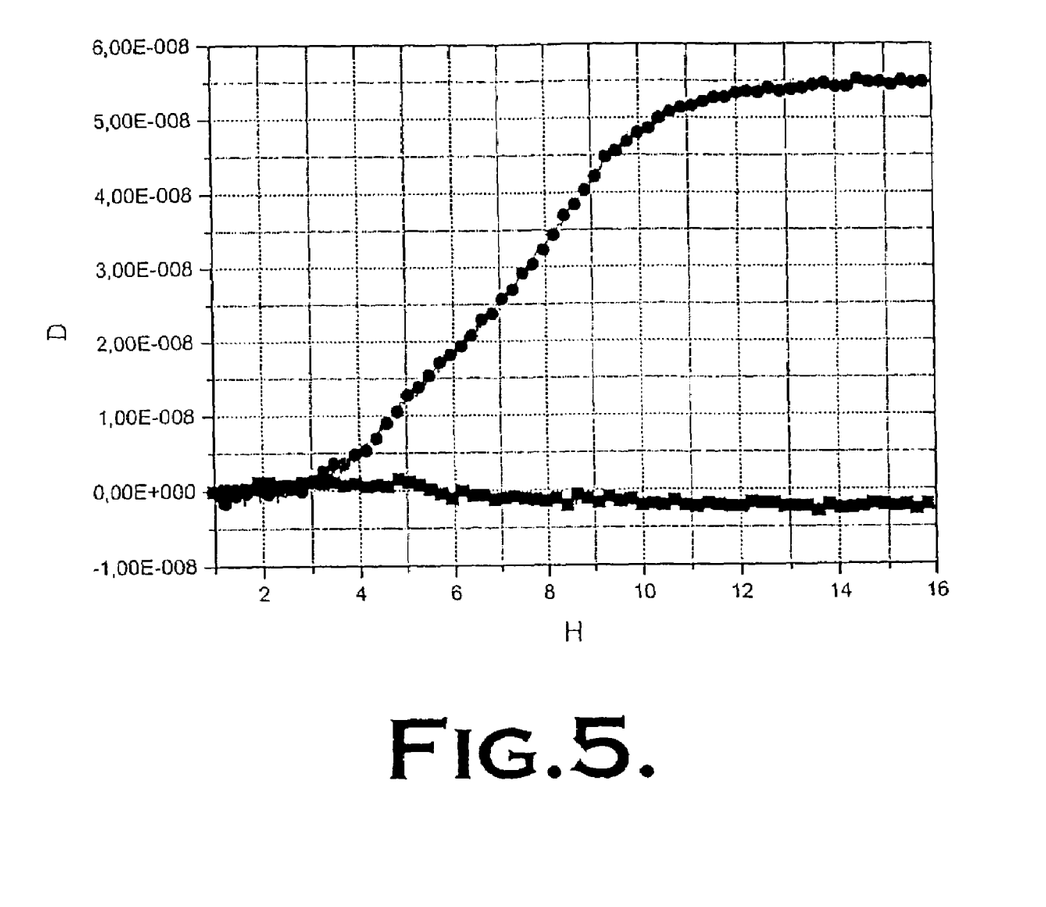

FIG. 5 shows the delay of the ultrasonic signal after traversing UHT concentrated orange juice (squares) and natural frozen orange juice after thawing thereof (circles). The H axis corresponds to the measurement time in hours and the R axis to the delay in seconds of the signal time-of-flight related to the time-of-flight of the initial signal.

Figure 6:
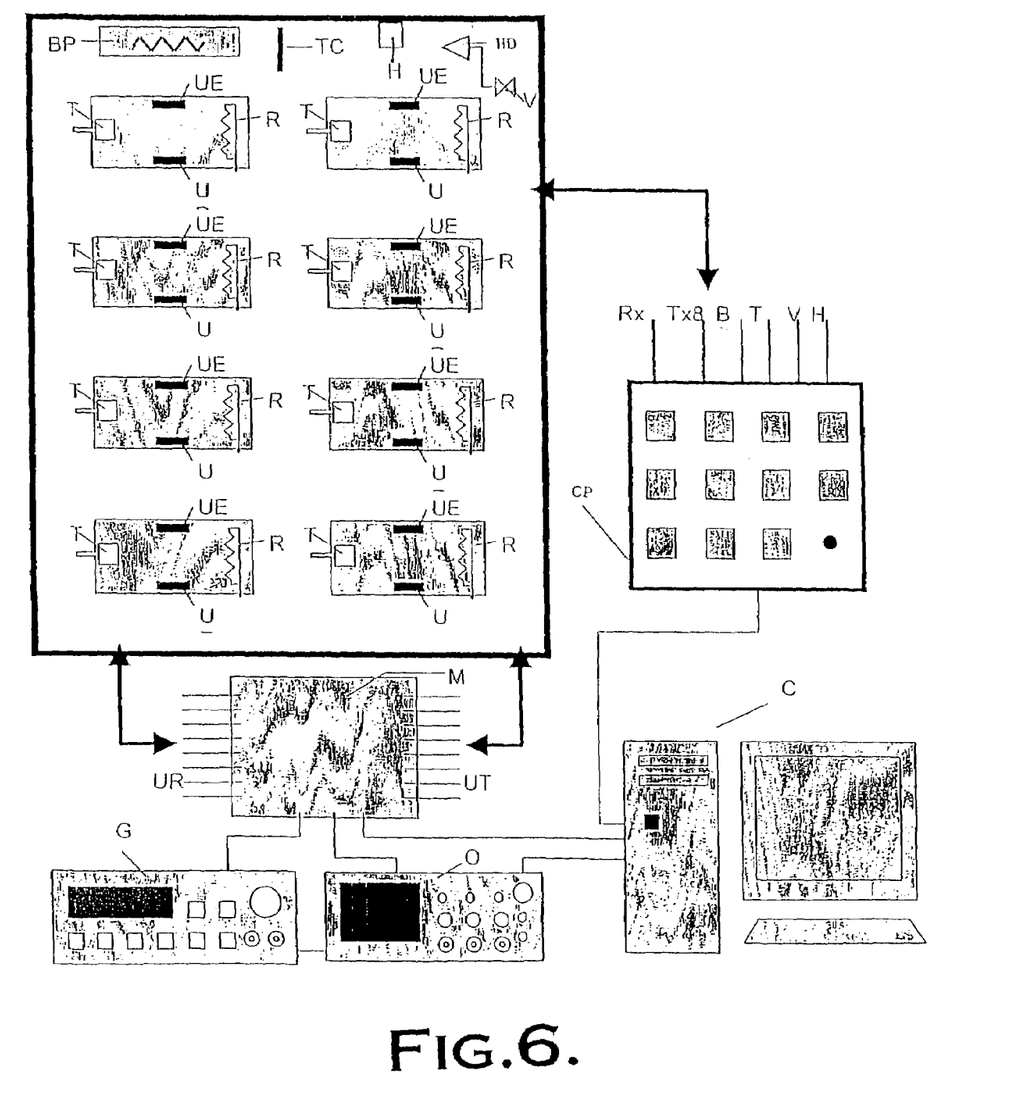

FIG. 6 shows the general scheme of the 8-channel ultrasonic device for the detection of microorganisms in milk packaged in Combibloc. In the main body, it can be seen the 8 housings in which the milk containers are introduced. Coupled to each housing there is an emission transducer -UE-, a reception transducer -UR-, a heating resistor -R- and a temperature sensor -T. In addition to the latter, there is also a general chamber temperature sensor -TC-, a Peltier pump—PP-, a humidity sensor -H-, and a humidity diffuser -HD- controlled by the electrovalve V. All these humidity and temperature systems are connected to the control panel -CP-, which in turn is communicated with the control computer -C- through RS -485. The ultrasonic transducers are connected to the multiplexer -M- which alternatively feeds each measurement channel. The electrical emission signal coming from the signal generator -G- reaches this multiplexer, and it sends the reception signal to the oscilloscope -O-, which in turn is communicated through GPIB with the computer -C- to capture the data. The multiplexer operation is also controlled by said computer through RS -232.

Figure 7:
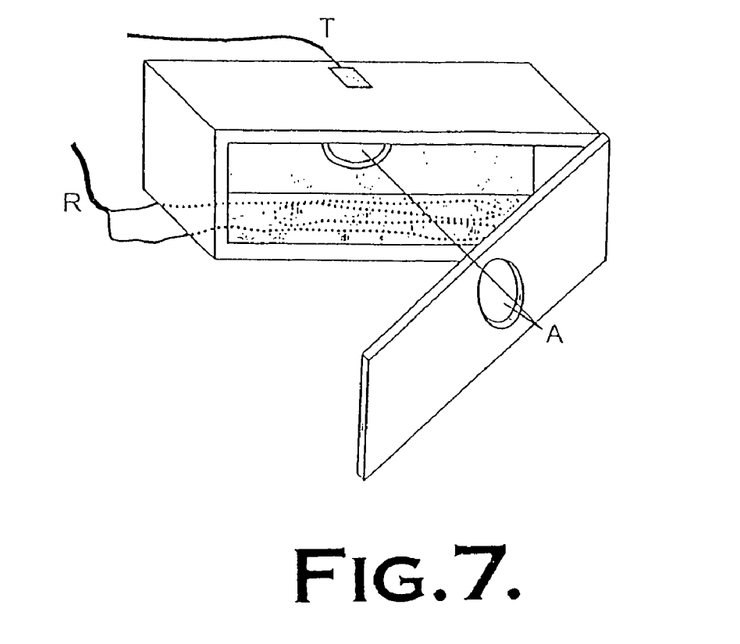

FIG. 7 shows the aluminum housing in which the containers are inserted in order to be analyzed. In the figure, the resistor -R- which heats the samples is shown, as well as the temperature sensor -T-, which monitors this heating. The facing holes -A- through which the emission transducer and reception transducer are inserted, are also seen.

Figure 8:
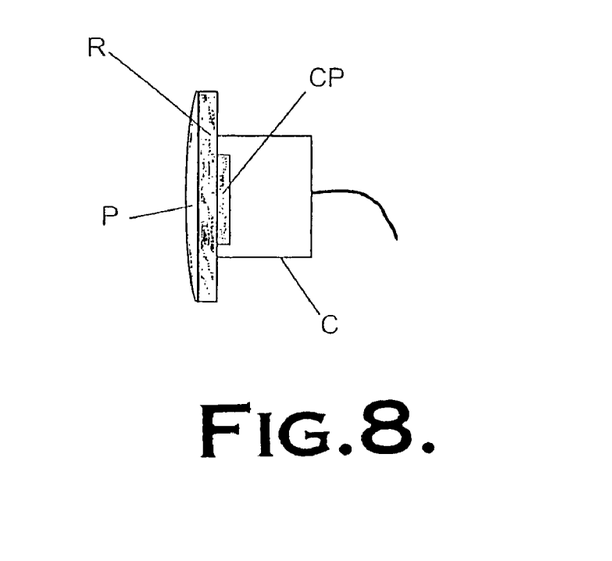

FIG. 8 shows a scheme of the type of transducer used for emission and reception of the ultrasonic waves. The piezoelectric ceramics -PC-, a delay line -D-, the polymeric mechanical coupling layer -P- and the transducer socket -B- are seen in this figure.

The invention claimed is:

1. An ultrasonic device for the noninvasive detection of the presence of microorganisms in foods, comprising a measurement chamber sized and shaped for receiving a sealed container holding said food, temperature and humidity control systems continuously measuring the temperature and humidity in the chamber and maintaining the temperature and humidity in the chamber at preselected levels, an elastic wave emitter system, an elastic wave receiver system, said emitter and receiver systems having an adaptation layer for dry coupling with the container, generation and reception electronic systems for the elastic wave emitter and receiver systems, and a computer system operably receiving and analyzing elastic wave data from said receiver system after passing through a container so as to control microbiological detection within the food.

2. An ultrasonic device for detecting microorganisms in food in multiple containers according to claim 1, wherein the measurement chamber is provided with passive hygroscopic and thermal isolation elements as well as individual housings for each container.

3. The ultrasonic device according to claim 1, wherein the humidity control system has a humidity measurement sensor and an actuator that operably enables regulating the humidity within precision of one point of relative humidity within the chamber and communication with the computer system.

4. The ultrasonic device according to claim 2, wherein the ultrasonic emission and receiver systems have at least one emission transducer and another reception transducer in emission-reception configuration for each housing, in a range between 100 kHz and 2 MHZ, said transducers each being provided with a layer of an elastic polymer adapted to engage a respective container in each housing to obtain a good mechanical adaptation to a respective container, electronic equipment for feeding and receiving a signal of each of said transducers, and communicate with the computer system.

5. The ultrasonic device according to claim 2 wherein the ultrasonic emission and receiver systems have has at least one emission and reception transducer in pulse-echo configuration for each container, in a range between 100 kHz and 2 MHZ, said transducers being provided with a layer of an elastic polymer adapted to engage a respective container to obtain a good mechanical adaptation to a respective container, electronic equipment for feeding and receiving a signal of said transducers, and communicate with the computer system.

6. The ultrasonic device according to claim 2 wherein the computer system has at least one computer capable of communicating with the transducers and includes control software capable of managing the measurement process and analyzing information received from the transducers to determine the presence of microorganisms inside each container.

7. The ultrasonic device according to claim 1 wherein the temperature control system has measurement sensors to measure the general temperature inside of the chamber and individual temperature of each container, actuators for regulating the general temperature of the chamber and the individual temperature of each container within a precision of 0.01° C. of the preselected temperature thereof and the communicates with the computer system.

8. A non invasive process for the detection of the presence of microorganisms in food comprising the steps of:
    placing the food in a sealed container; and thereafter placing the container in a testing chamber;
    controlling the temperature in the chamber to a preselected temperature;
    controlling the humidity in the chamber to a preselected humidity;
    dry coupling an elastic wave emitter system to the container;
    providing an elastic wave receiver system in contact with the container;
    thereafter utilizing the wave emitter system to transmit elastic waves through the container to the elastic wave receiver system; and
    analyzing the elastic waves received by the elastic wave receiver system to determine the presence of microorganisms in the food.

9. The process according to claim 8 including the step of providing a single electromechanical transducer that receives elastic waves in the receiver system and transmits elastic waves from the emitter system such that the elastic wave after traversing the medium is reflected at the opposite side of the container and received by the receiver system.

10. The process according to claim 8 including the step of discriminating the type of microorganism responsible for the contamination of the food according to the relative variations of the propagation speed, the attenuation and the distortion of the elastic wave.

11. The process according to claim 8 wherein the food is milk.

12. The process according to claim 8 wherein said container is subject to deterioration by water and including the step of:

maintaining said container dry throughout the process.

13. The process according to claim 8 including the step of constructing said container of a paper product.

* * * * *